(12) United States Patent
Lee

(10) Patent No.: US 7,053,184 B2
(45) Date of Patent: May 30, 2006

(54) PURIFIED HUMAN ERYTHROPOIETIN RECEPTOR PROTEIN FRAGMENT AND ANTIBODIES DERIVED THEREFROM

(76) Inventor: Jong Y. Lee, 514 Huron Blvd. SE. #A-11, Minneapolis, MN (US) 55414

(*) Notice: Subject to any disclaimer, the term of this patent is extended or adjusted under 35 U.S.C. 154(b) by 0 days.

(21) Appl. No.: 09/016,159

(22) Filed: Jan. 30, 1998

(65) Prior Publication Data

US 2002/0031806 A1 Mar. 14, 2002

Related U.S. Application Data

(60) Continuation of application No. 08/876,227, filed on Jun. 16, 1997, now abandoned, which is a continuation of application No. 08/734,097, filed on Oct. 21, 1996, now abandoned, which is a continuation of application No. 08/460,525, filed on Jun. 2, 1995, now abandoned, which is a division of application No. 08/106,815, filed on Aug. 16, 1993, now abandoned.

(51) Int. Cl.
*A61K 38/19* (2006.01)
*A61K 38/17* (2006.01)
*C07K 14/00* (2006.01)
*G01N 33/53* (2006.01)

(52) U.S. Cl. .................. 530/351; 435/7.1
(58) Field of Classification Search ........... 530/350; 435/7.1
See application file for complete search history.

(56) References Cited

U.S. PATENT DOCUMENTS 5,378,808 A * 1/1995 D'Andrea, et al. ......... 530/350

OTHER PUBLICATIONS

Harris, K. W., et al. (1992) *J. Biol. Chem.* 267: 15205-09.*
Elliot et al. Activation of the EPO Receptor by Bivalent anti-EPO-Receptor Antibodies. Journal of Biological Chemistry. vol. 271, No. 40. Oct. 1996, pp. 24691-24697.*
Sambrook et al. Molecular Cloning, vol. 3, (pp. 16.3-16.5, 16.17-16.18)). 1989.*
Jones et al. Human Erythropoietin Receptor: Cloning, Expression, and Biologic Characterization. Blood, vol. 76, No. 1, Jul. 1990, pp. 31-35.*

* cited by examiner

*Primary Examiner*—Joseph Murphy
*Assistant Examiner*—Fozia Hamud
(74) *Attorney, Agent, or Firm*—Hugh McTavish

(57) ABSTRACT

A *E. coli* recombinant plasmid expressing a fusion protein having the human erythropoietin receptor extracellular domain is disclosed. A purified fusion protein produced from such a vector is also disclosed, the fusion protein having a cleavage site suitable for separating the erythropoietin receptor extracellular domain from the remainder of the fusion protein. Antibodies having specific binding affinity for a purified extracellular domain polypeptide are also disclosed. The purified human erythropoietin receptor fragment polypeptide binds erythropoietin. The articles, compositions and methods of the invention are useful for studying ligand binding to erythropoietin receptor and for quantitating the amounts of erythropoietin receptor, as well as for understanding receptor structure and signal transduction.

5 Claims, 6 Drawing Sheets

Fig. 4

MW
kDa 58.1 —  ▬                    EpoRex-th 39.8 ●

29.0 ●   ▬  —  ◉  Epo-bp
                  GST 14.3 ●

1  2  3  4

```
                            SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (ix) FEATURE:
        (A) NAME/KEY: BamH1 linker at 5' end  followed by sequence for
            amino acids 25 through 29 of the full length human Epor
            protein.  Forward primer for Sequence ID No. 2."

(xi) SEQUENCE DESCRIPTION: SEQ ID NO:1:

TTGGATCC GCG CCC CCG CCT  A AC                                         23
         Ala Pro Pro Pro
          1

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (ix) FEATURE:
        (A) NAME/KEY: EcoR1 linker followed by sequence complementary
            to coding sequence for amino acids 226 through 222 of full
            length human EpoR protein.  Reverse primer for Sequence ID
            No. 1.

(xi) SEQUENCE DESCRIPTION: SEQ ID NO:2:

TGAATTCGGG GTCCAGGTCG CT                                               22

(2) INFORMATION FOR SEQ ID NO:3:

(i) SEQUENCE CHARACTERISTICS:
        (A) LENGTH: 18 base pairs
        (B) TYPE: nucleic acid
```

```
            (C) STRANDEDNESS: double
            (D) TOPOLOGY: linear (ii) MOLECULE TYPE: other nucleic acid (iii) HYPOTHETICAL: NO (iv) ANTI-SENSE: NO (vi) ORIGINAL SOURCE:
            (A) ORGANISM: Homo sapiens (vii) IMMEDIATE SOURCE:
            (B) CLONE: pGEX-2T, Pharmacia (Mechanicsburg, PA)

(ix) FEATURE:
            (A) NAME/KEY: Thrombin Cleavage Site in plasmid vector
                pGEX-2T."

(x) PUBLICATION INFORMATION:
            (A) AUTHORS: Smith, D.B.
                   Johnson, K.S.
            (B) TITLE: Single-step purification of polypeptides
                   expressed in Escherichia coli as fusions with
                   glutathione-S-transferase
            (D) VOLUME: 67
            (F) PAGES: 31-40
            (G) DATE: 1988

(xi) SEQUENCE DESCRIPTION: SEQ ID NO:3:

CTG GTT CCG CGT GGA  TCC                                                18
Leu Val Pro Arg Gly Ser
                10

(2) INFORMATION FOR SEQ ID NO:4:

(i) SEQUENCE CHARACTERISTICS:
            (A) LENGTH: 1527 base pairs
            (B) TYPE: nucleic acid
            (C) STRANDEDNESS: double
            (D) TOPOLOGY: linear (x) PUBLICATION INFORMATION:
            (A) AUTHORS: Winkelmann , J. C., et al.
            (C) JOURNAL: Blood
            (D) VOLUME: 76
            (E) ISSUE: 1
            (F) PAGES: 24-30
            (G) DATE: 1990

(x) PUBLICATION INFORMATION:
            (A) AUTHORS: Jones, S.S., et al.
            (C) JOURNAL: Blood
            (D) VOLUME: 76
            (E) ISSUE: 1
            (F) PAGES: 31-35
            (G) DATE: 1990

(x) PUBLICATION INFORMATION:
            (A) AUTHORS: Noguchi, C.T., et al.
            (C) JOURNAL: Blood
            (D) VOLUME: 78
            (E) ISSUE: 10
            (F) PAGES: 2548-2556
            (G) DATE: 1991

(xi) SEQUENCE DESCRIPTION: SEQ ID NO:4:

ATG GAC CAC CTC GGG GCG TCC CTC TGG CCC CAG GTC GGC TCC CTT TGT        48
Met Asp His Leu Gly Ala Ser Leu Trp Pro Gln Val Gly Ser Leu Cys
  1               5                  10                  15

CTC CTG CTC GCT GGG GCC GCC TGG GCG CCC CCG CCT AAC CTC CCG GAC        96
Leu Leu Leu Ala Gly Ala Ala Trp Ala Pro Pro Pro Asn Leu Pro Asp
            20                  25                  30

CCC AAG TTC GAG AGC AAA GCG GCC TTG CTG GCG GCC CGG GGG CCC GAA       144
```

-continued

```
Pro Lys Phe Glu Ser Lys Ala Ala Leu Leu Ala Ala Arg Gly Pro Glu
         35                  40                  45

GAG CTT CTG TGC TTC ACC GAG CGG TTG GAG GAC TTG GTG TGT TTC TGG       192
Glu Leu Leu Cys Phe Thr Glu Arg Leu Glu Asp Leu Val Cys Phe Trp
 50                  55                  60

GAG GAA GCG GCG AGC GCT GGG GTG GGC CCG GGC AAC TAC AGC TTC TCC       240
Glu Glu Ala Ala Ser Ala Gly Val Gly Pro Gly Asn Tyr Ser Phe Ser
 65                  70                  75                  80

TAC CAG CTC GAG GAT GAG CCA TGG AAG CTG TGT CGC CTG CAC CAG GCT       288
Tyr Gln Leu Glu Asp Glu Pro Trp Lys Leu Cys Arg Leu His Gln Ala
                 85                  90                  95

CCC ACG GCT CGT GGT GCG GTG CGC TTC TGG TGT TCG CTG CCT ACA GCC       336
Pro Thr Ala Arg Gly Ala Val Arg Phe Trp Cys Ser Leu Pro Thr Ala
            100                 105                 110

GAC ACG TCG AGC TTC GTG CCC CTA GAG TTG CGC GTC ACA GCA GCC TCC       384
Asp Thr Ser Ser Phe Val Pro Leu Glu Leu Arg Val Thr Ala Ala Ser
            115                 120                 125

GGC GCT CCG CGA TAT CAC CGT GTC ATC CAC ATC AAT GAA GTA GTG CTC       432
Gly Ala Pro Arg Tyr His Arg Val Ile His Ile Asn Glu Val Val Leu
130                 135                 140

CTA GAC GCC CCC GTG GGG CTG GTG GCG CGG TTG GCT GAC GAG AGC GGC       480
Leu Asp Ala Pro Val Gly Leu Val Ala Arg Leu Ala Asp Glu Ser Gly
145                 150                 155                 160

CAC GTA GTG TTG CGC TGG CTC CCG CCG CCT GAG ACA CCC ATG ACG TCT       528
His Val Val Leu Arg Trp Leu Pro Pro Pro Glu Thr Pro Met Thr Ser
                165                 170                 175

CAC ATC CGC TAC GAG GTG GAC GTC TCG GCC GGC AAC GGC GCA GGG AGC       576
His Ile Arg Tyr Glu Val Asp Val Ser Ala Gly Asn Gly Ala Gly Ser
            180                 185                 190

GTA CAG AGG GTG GAG ATC CTG GAG GGC CGC ACC GAG TGT GTG CTG AGC       624
Val Gln Arg Val Glu Ile Leu Glu Gly Arg Thr Glu Cys Val Leu Ser
            195                 200                 205

AAC CTG CGG GGC CGG ACG CGC TAC ACC TTC GCC GTC CTC GCG CGT ATG       672
Asn Leu Arg Gly Arg Thr Arg Tyr Thr Phe Ala Val Leu Ala Arg Met
210                 215                 220

GCT GAG CCG AGC TTC GGC GGC TTC TGG AGC GCC TGG TCG GAG CCT GTG       720
Ala Glu Pro Ser Phe Gly Gly Phe Trp Ser Ala Trp Ser Glu Pro Val
225                 230                 235                 240

TCG CTG CTG ACG CCT AGC GAC CTG GAC CCC CTC ATC CTG ACG CTC TCC       768
Ser Leu Leu Thr Pro Ser Asp Leu Asp Pro Leu Ile Leu Thr Leu Ser
                245                 250                 255

CTC ATC CTC GTG GTC ATC CTG GTG CTG CTG ACC GTG CTC GCG CTG CTC       816
Leu Ile Leu Val Val Ile Leu Val Leu Leu Thr Val Leu Ala Leu Leu
            260                 265                 270

TCC CAC CGC CGG GCT CTG AAG CAG AAG ATC TGG CCT GGC ATC CCG AGC       864
Ser His Arg Arg Ala Leu Lys Gln Lys Ile Trp Pro Gly Ile Pro Ser
            275                 280                 285

CCA GAG AGC GAG TTT GAA GGC CTC TTC ACC ACC CAC AAG GGT AAC TTC       912
Pro Glu Ser Glu Phe Glu Gly Leu Phe Thr Thr His Lys Gly Asn Phe
            290                 295                 300

CAG CTG TGG CTG TAC CAG AAT GAT GGC TGC CTG TGG TGG AGC CCC TGC       960
Gln Leu Trp Leu Tyr Gln Asn Asp Gly Cys Leu Trp Trp Ser Pro Cys
305                 310                 315                 320

ACC CCC TTC ACG GAG GAC CCA CCT GCT TCC CTG GAA GTC CTC TCA GAG      1008
Thr Pro Phe Thr Glu Asp Pro Pro Ala Ser Leu Glu Val Leu Ser Glu
                325                 330                 335

CGC TGC TGG GGG ACG ATG CAG GCA GTG GAG CCG GGG ACA GAT GAT GAG      1056
Arg Cys Trp Gly Thr Met Gln Ala Val Glu Pro Gly Thr Asp Asp Glu
            340                 345                 350
```

-continued

```
GGC CCC CTG CTG GAG CCA GTG GGC AGT GAG CAT GCC CAG GAT ACC TAT        1104
Gly Pro Leu Leu Glu Pro Val Gly Ser Glu His Ala Gln Asp Thr Tyr
        355                 360                 365

CTG GTG CTG GAC AAA TGG TTG CTG CCC CGG AAC CCG CCC AGT GAG GAC        1152
Leu Val Leu Asp Lys Trp Leu Leu Pro Arg Asn Pro Pro Ser Glu Asp
370                 375                 380

CTC CCA GGG CCT GGT GGC AGT GTG GAC ATA GTG GCC ATG GAT GAA GGC        1200
Leu Pro Gly Pro Gly Gly Ser Val Asp Ile Val Ala Met Asp Glu Gly
385                 390                 395                 400

TCA GAA GCA TCC TCC TGC TCA TCT GCT TTG GCC TCG AAG CCC AGC CCA        1248
Ser Glu Ala Ser Ser Cys Ser Ser Ala Leu Ala Ser Lys Pro Ser Pro
                405                 410                 415

GAG GGA GCC TCT GCT GCC AGC TTT GAG TAC ACT ATC CTG GAC CCC AGC        1296
Glu Gly Ala Ser Ala Ala Ser Phe Glu Tyr Thr Ile Leu Asp Pro Ser
            420                 425                 430

TCC CAG CTC TTG CGT CCA TGG ACA CTG TGC CCT GAG CTG CCC CCT ACC        1344
Ser Gln Leu Leu Arg Pro Trp Thr Leu Cys Pro Glu Leu Pro Pro Thr
        435                 440                 445

CCA CCC CAC CTA AAG TAC CTG TAC CTT GTG GTA TCT GAC TCT GGC ATC        1392
Pro Pro His Leu Lys Tyr Leu Tyr Leu Val Val Ser Asp Ser Gly Ile
450                 455                 460

TCA ACT GAC TAC AGC TCA GGG GAC TCC CAG GGA GCC CAA GGG GGC TTA        1440
Ser Thr Asp Tyr Ser Ser Gly Asp Ser Gln Gly Ala Gln Gly Gly Leu
465                 470                 475                 480

TCC GAT GGC CCC TAC TCC AAC CCT TAT GAG AAC AGC CTT ATC CCA GCC        1488
Ser Asp Gly Pro Tyr Ser Asn Pro Tyr Glu Asn Ser Leu Ile Pro Ala
                485                 490                 495

GCT GAG CCT CTG CCC CCC AGC TAT GTG GCT TGC TCT TAG                    1527
Ala Glu Pro Leu Pro Pro Ser Tyr Val Ala Cys Ser
            500                 505
```

(2) INFORMATION FOR SEQ ID NO:5:

(i) SEQUENCE CHARACTERISTICS:
        (A) LENGTH: 508 amino acids
        (B) TYPE: amino acid
        (D) TOPOLOGY: linear (ii) MOLECULE TYPE: protein (xi) SEQUENCE DESCRIPTION: SEQ ID NO:5:

```
Met Asp His Leu Gly Ala Ser Leu Trp Pro Gln Val Gly Ser Leu Cys
1               5                   10                  15

Leu Leu Leu Ala Gly Ala Ala Trp Ala Pro Pro Asn Leu Pro Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
    50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
    130                 135                 140
```

-continued

```
Leu Asp Ala Pro Val Gly Leu Val Ala Arg Leu Ala Asp Glu Ser Gly
145                 150                 155                 160

His Val Val Leu Arg Trp Leu Pro Pro Glu Thr Pro Met Thr Ser
        165                 170                 175

His Ile Arg Tyr Glu Val Asp Val Ser Ala Gly Asn Gly Ala Gly Ser
                180                 185                 190

Val Gln Arg Val Glu Ile Leu Glu Gly Arg Thr Glu Cys Val Leu Ser
            195                 200                 205

Asn Leu Arg Gly Arg Thr Arg Tyr Thr Phe Ala Val Leu Ala Arg Met
210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
            260                 265                 270

Ser His Arg Arg Ala Leu Lys Gln Lys Ile Trp Pro Gly Ile Pro Ser
        275                 280                 285

Pro Glu Ser Glu Phe Glu Gly Leu Phe Thr Thr His Lys Gly Asn Phe
    290                 295                 300

Gln Leu Trp Leu Tyr Gln Asn Asp Gly Cys Leu Trp Trp Ser Pro Cys
305                 310                 315                 320

Thr Pro Phe Thr Glu Asp Pro Pro Ala Ser Leu Glu Val Leu Ser Glu
                325                 330                 335

Arg Cys Trp Gly Thr Met Gln Ala Val Glu Pro Gly Thr Asp Asp Glu
            340                 345                 350

Gly Pro Leu Leu Glu Pro Val Gly Ser Glu His Ala Gln Asp Thr Tyr
        355                 360                 365

Leu Val Leu Asp Lys Trp Leu Leu Pro Arg Asn Pro Pro Ser Glu Asp
    370                 375                 380

Leu Pro Gly Pro Gly Gly Ser Val Asp Ile Val Ala Met Asp Glu Gly
385                 390                 395                 400

Ser Glu Ala Ser Ser Cys Ser Ser Ala Leu Ala Ser Lys Pro Ser Pro
                405                 410                 415

Glu Gly Ala Ser Ala Ala Ser Phe Glu Tyr Thr Ile Leu Asp Pro Ser
            420                 425                 430

Ser Gln Leu Leu Arg Pro Trp Thr Leu Cys Pro Glu Leu Pro Pro Thr
        435                 440                 445

Pro Pro His Leu Lys Tyr Leu Tyr Leu Val Val Ser Asp Ser Gly Ile
    450                 455                 460

Ser Thr Asp Tyr Ser Ser Gly Asp Ser Gln Gly Ala Gln Gly Gly Leu
465                 470                 475                 480

Ser Asp Gly Pro Tyr Ser Asn Pro Tyr Glu Asn Ser Leu Ile Pro Ala
                485                 490                 495

Ala Glu Pro Leu Pro Pro Ser Tyr Val Ala Cys Ser
            500                 505
```

PURIFIED HUMAN ERYTHROPOIETIN RECEPTOR PROTEIN FRAGMENT AND ANTIBODIES DERIVED THEREFROM

This application is a continuation of U.S. application Ser. No. 08/876,227, filed Jun. 16, 1997, abandoned which is a continuation of U.S. application Ser. No. 08/734,097, filed Oct. 21, 1996, abandoned which is a continuation of U.S. application Ser. No. 08/460,525, filed Jun. 2, 1995, abandoned which is a divisional of U.S. application Ser. No. 08/106,815, filed Aug. 16, 1993 abandoned.

FIELD OF THE INVENTION

This invention relates to purified human erythropoietin receptor extracellular domain polypeptide. More particularly, this invention relates to human erythropoietin receptor extracellular domain polypeptide that retains affinity for erythropoietin, to DNA sequences suitable for use in producing such a polypeptide, and to antibodies recognizing such a polypeptide.

BACKGROUND OF THE INVENTION

Erythropoietin (Epo) is a glycoprotein hormone of molecular weight 34 kilodaltons (kDa) that is produced in the mammalian kidney and liver. Epo is a key component in erythropoiesis, inducing the proliferation and differentiation of red cell progenitors. Epo activity also is associated with the activation of a number of erythroid-specific genes, including globin and carbonic anhydrase. Bondurant et al., *Mol. Cell Biol.* 5:675–683 (1985); Koury et al., *J. Cell. Physiol.* 126:259–265 (1986). The erythropoietin receptor (EpoR) is a member of the hematopoietic/cytokine/growth factor receptor family, which includes several other growth factor receptors, such as the interleukin (IL)-3,-4 and -6 receptors, the granulocyte macrophage colony-stimulating factor (GM-CSF) receptor as well as the prolactin and growth hormone receptors. Bazan, *Proc. Natl. Acad. Sci USA* 87:6934–6938 (1990). Members of the cytokine receptor family contain four conserved residues and a tryptophan-serine-X-tryptophan-serine motif positioned just outside the transmembrane region. The conserved sequences are thought to be involved in protein-protein interactions. Chiba et al., *Biochim. Biophys. Res. Comm.* 184:485–490 (1992).

EpoR cDNA has been isolated recently from mouse liver, Tojo et al., *Biochem. Biophys. Res. Comm.* 148: 443–48 (1987) and from human fetal liver. Jones et al., *Blood* 76:31–35 (1990); Winkelmann et al., *Blood* 76:24–30 (1990). The full length EpoR cDNA sequence is shown in the Sequence Listing as SEQ ID NO: 4. The human cDNA encodes a polypeptide chain of MW about 55 kDa and having about 508 amino acids. The polypeptide encoded by SEQ ID NO:4 is SEQ ID NO:5. Genomic clones of human EpoR have been isolated and sequenced. Penny and Forget, *Genomics* 11:974–80(1991); Noguchi et al., *Blood* 78:2548–2556 (1991). Analysis of the coding sequence predicts about 24 amino acid residues in a signal peptide, about 226 amino acids in an extracellular domain, about 23 amino acids in a membrane-spanning domain, and about 235 amino acids in a cytoplasmic domain. D'Andrea and Zon, *J. Clin. Invest.* 86:681–687 (1990); Jones et al., *Blood* 76:31–35, (1990); Penny and Forget, *Genomics* 11: 974–80 (1991). The mature human EpoR protein has about 484 amino acids. All human erythroid progenitor cells have been shown to contain Epo receptors. Binding of Epo appears to decline as erythroid progenitor cells mature, until Epo receptors are not detectable on reticulocytes. Sawada et al., *J. Clin. Invest.* 80:357–366 (1987). Sawada et al., *J. Cell. Physiol.* 137:337 (1988). Epo maintains the cellular viability of the erythroid progenitor cells and allows them to proceed with mitosis and differentiation. Two major erythroid progenitors responsive to Epo are the Burst-forming units-erythroid (BFU-E) and the Colony-forming units-erythroid (CFU-E). The Epo receptor number correlates very well with the response to Epo in normal BFU-E and CFU-E. Epo receptor numbers appear to decline after reaching the peak receptor number at the CFU-E stage in human and murine cells. Sawada et al., *J. Clin. Invest.* 80:357–366 (1987); Landschulz et al., *Blood* 73:1476–1486 (1989). The recovery of Epo receptors after removal of Epo appears to be dependent on protein synthesis, which suggests downregulation of Epo receptor by degradation, and the subsequent upregulation of receptors by the new synthesis of receptors when Epo is removed. Sawyer and Hankins, *Blood* 72:132 (1988). Studies of Epo receptors on megakaryocytes and erythroid progenitors suggest that there is a link between the regulation of erythropoiesis and thrombopoiesis, in that stimulation of cell division by both cell types is controlled by Epo receptor numbers. Berridge et al., *Blood* 72:970–977 (1988). Although the Epo receptor has been cloned, the precise mechanisms involved in binding of Epo to Epo receptors and the relationship to subsequent erythropoietic processes are not known.

Characterization of the Epo receptor (EpoR) has been difficult due to the extremely small quantities of EpoR that can be obtained from natural sources. Thus, the mechanism of Epo interaction with its receptor, which stimulates erythropoiesis, is still unknown. D'Andrea and Zon, *J. Clin. Invest.* 86:681–687 (1990). Recently this mechanism has been of great interest in understanding the role of growth factors and their receptors in leukemogenesis; altered hematopoietic growth factors and their receptors may contribute to tumorigenesis and leukemogenesis. Dunbar et al., *Science* 245:1493–1496 (1989); Li et al., *J. Virol.* 57:534–538 (1986).

Several studies of the correlation between the Epo responsiveness of a particular cell type and the affinity of the cell type for Epo have reported discordant results. These studies have used recombinant Epo or EpoR possessing some non-native amino acid sequence from the corresponding plasmid vectors. Berridge et al., *Blood* 72:970–977 (1988); Harris et al., *J. Biol. Chem.* 267: 15205–09 (1992). It is possible that tertiary structural changes and/or other features of these recombinant Epo or EpoR molecules have changed the characteristics of the native protein. Thus, it would be a significant advance to obtain substantially pure fragments of the Epo receptor, free of extraneous (e.g, vector) amino acid sequence. Although it could not be predicted whether or not such fragments would retain functional activity, nevertheless a purified extracellular domain fragment would be particularly useful since Epo binds to the extracellular domain of the Epo receptor.

SUMMARY OF THE INVENTION

An expression vector is disclosed, comprising a first nucleotide sequence capable of expressing a polypeptide that has a thrombin proteolytic cleavage site near the carboxyl terminus and a second nucleotide sequence consisting essentially of nucleotides 73 to 750 of a full length human erythropoietin receptor cDNA coding sequence. The Epo receptor cDNA coding sequence fragment is positioned 3' to (downstream of) the proteolytic cleavage site and is in the same translational reading frame as the proteolytic cleavage site. The Epo receptor cDNA coding sequence fragment is oriented to be translationally contiguous with the first polynucleotide sequence.

A purified fusion protein is disclosed, comprising a first segment consisting essentially of a polypeptide produced by an expression vector and having a thrombin proteolytic cleavage site, and a second segment consisting essentially of about amino acid 25 to about amino acid 250 of the full length human erythropoietin receptor protein. The second segment is covalently coupled to the carboxyl end of the first segment. A purified protein, consisting essentially of about amino acid 25 to about amino acid 250 of the full length human erythropoietin receptor protein sequence, may be produced by thrombin cleavage of the fusion protein.

An antibody having affinity for a purified human erythropoietin receptor polypeptide extracellular domain is disclosed. The antibody has affinity for a polypeptide comprising about amino acid 25 to about amino acid 250 of the full length human erythropoietin receptor protein sequence.

An immunoassay composition comprising a solid phase reagent and the antibody operably coupled to the solid phase reagent, is disclosed. Also disclosed is an immunoassay composition comprising a solid phase reagent and the purified protein operably coupled to the solid phase reagent.

Methods for obtaining a substantially pure human erythropoietin receptor polypeptide consisting essentially of about amino acid 25 to about amino acid 250 of the full length human erythropoietin receptor protein are disclosed. The substantially pure human erythropoietin receptor polypeptide retains the ability to bind specifically to erythropoietin. The methods include treating the fusion protein with thrombin under conditions allowing cleavage of the polypeptide from the fusion protein, to form a digest mixture; adding the digest mixture to a solid phase reagent having erythropoietin coupled thereto, under conditions allowing binding of the polypeptide with the solid phase reagent, to form a polypeptide-solid phase composition; washing the polypeptide-solid phase composition to remove unbound material; and eluting the substantially pure human erythropoietin receptor polypeptide from the polypeptide-solid phase composition.

BRIEF DESCRIPTION OF THE FIGURES

FIG. 1 also depicts the recombinant fusion protein, EpoRex-th, that is expressed from pJYL26.

FIG. 4 is a Western blot, showing binding of sheep anti-Epo-bp antibody to Epo-bp.

DETAILED DESCRIPTION OF THE INVENTION

Figure 1:
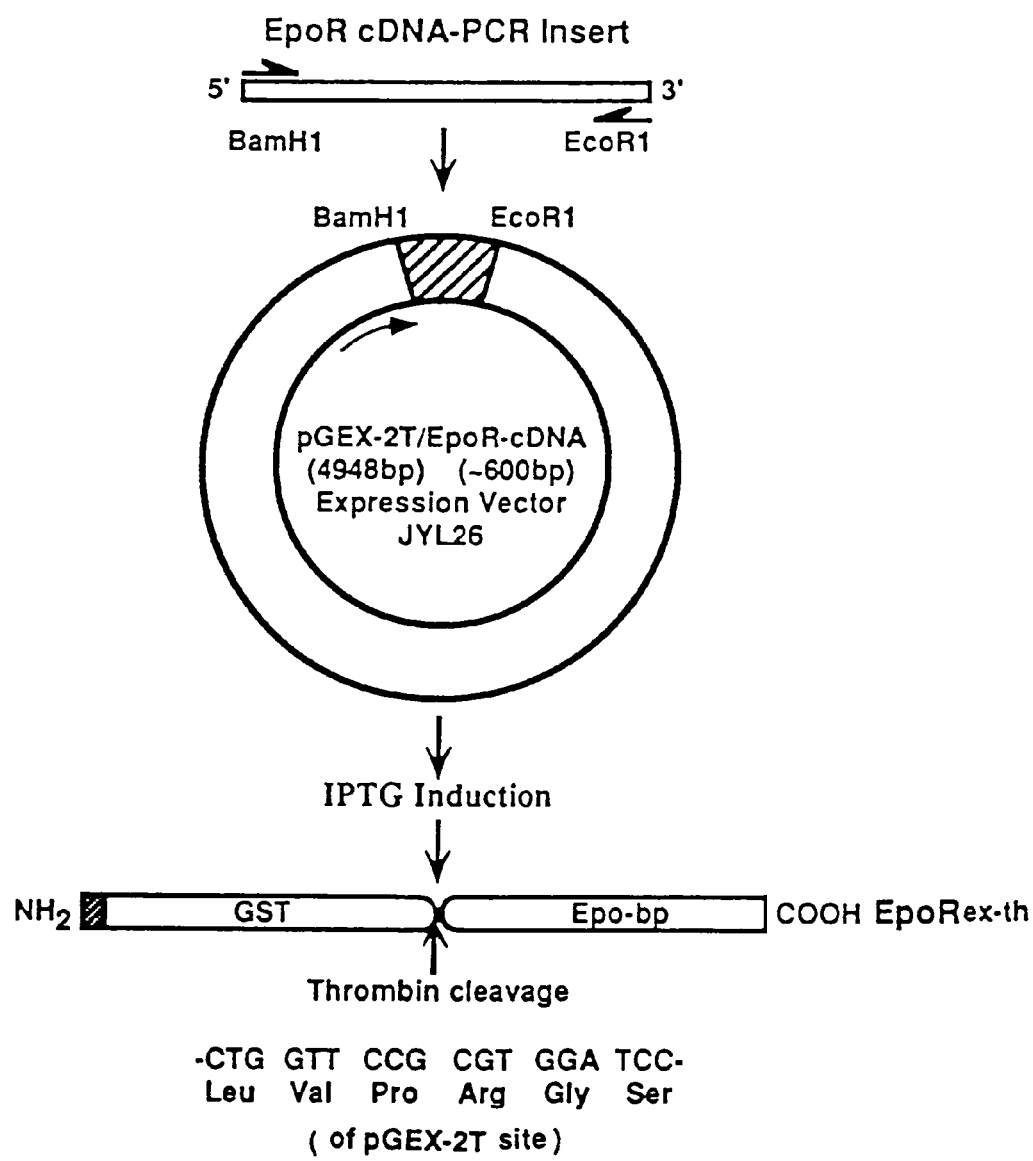
FIG. 1 is a diagrammatic representation of pJYL26, a plasmid having about 678 bp of the 5' coding sequence of human erythropoietin receptor cDNA inserted into the expression vector pGEX-2T.

Despite the availability of recombinant human Epo and full-length human Epo receptor cDNA clones, little is known about the interaction of Epo and Epo receptor, or the signal transducing mechanisms involved in proliferation and differentiation of erythroid progenitor cells.

Plasmid expression vectors permit expression of a protein from cloned coding sequences that have been inserted into the vector. Expression vectors generally have a selectable marker and a replication origin for selection and maintenance of the vector in a host cell, as well as inducible regulatory elements for inducing high level expression of a polypeptide suitable for fusing to an inserted gene. It is preferred that convenient restriction sites be engineered into the vector downstream from a proteolytic cleavage site sequence. A preferred polypeptide to be fused to the Epo coding sequence fragment is glutathione S-transferase, possessing a thrombin proteolytic cleavage site at the carboxyl terminus.

An expression vector for the invention disclosed herein expresses the EpoR extracellular domain as part of a fusion protein that can subsequently be cleaved to yield purified EpoR extracellular domain. The coding sequence for the EpoR extracellular domain may be engineered in any manner suitable for inserting the sequence in the appropriate reading frame in the expression vector. For example, a pair of polymerase chain reaction (PCR) primers may be synthesized, such that the first primer corresponds to the coding sequence at the 5' end of the extracellular domain and the second primer is complementary to the coding sequence of the 3' end of the extracellular domain. The primers preferably have convenient restriction enzyme sites flanking the portions of the primers corresponding to the ends of the desired target sequences. The primers are used to amplify the EpoR extracellular domain from a full length human EpoR cDNA template. The resulting PCR product is then cloned into an expression vector. It is preferable to synthesize PCR primers having different restriction sites at each end, rather than the same restriction site. The presence of different restriction sites at each end of the PCR product facilitates the insertion of the human EpoR coding sequence fragment in the sense orientation.

High level expression of a fusion protein having human erythropoietin receptor extracellular domain as part of the fusion protein is achieved by inducing expression from the recombinant plasmid expression vector in a host cell culture. A fusion protein is hereinafter referred to as EpoRex-th and a purified human erythropoietin receptor extracellular domain hereinafter is referred to as Epo-bp. A cell protein extract is preferably prepared from an expressing *E. coli* culture in any suitable manner. EpoRex-th may be purifed from the extract as desired. For example, the extract may be passed over a column having the ability to bind the portion of the fusion protein upstream of the Epo-bp coding sequence. The fusion protein will bind to the column, while other proteins in the extract are eluted in column washes with a buffer that allows binding of fusion protein to the column matrix. EpoRex-th can be subsequently eluted in high purity by changing the buffer conditions.

Purification of Epo-bp may be accomplished by cleaving purified EpoRex-th using an appropriate cleavage method.

For example, the cleavage site between the upstream polypeptide and Epo-bp may be sensitive to cyanogen bromide or, alternatively, may be sensitive to site-specific protease cleavage. In a preferred embodiment, a thrombin proteolytic cleavage site is engineered into the upstream polypeptide, but 5' to the convenient restriction cloning sites positioned at the carboxyl terminus of the upstream polypeptide coding sequence.

The cleaved Epo-bp polypeptide segment may be separated from the upstream polypeptide segment by purification techniques such as size exclusion chromatography, isoelectric focusing, or affinity chromatography. Furthermore, more than one purification technique may be used, if desired, to achieve the appropriate degree of purification. A preferred purification technique is affinity chromatography. For example, a protease-treated fusion protein mixture may be applied to a column having agarose beads coupled to Epo. The cleaved Epo-bp segment will bind to the Epo-agarose, while the upstream polypeptide segment will pass through the column. Epo-bp may then be eluted by lowering the pH of the liquid phase.

In an embodiment of the invention, the coding sequence for amino acids 25 through 250 of human EpoR (hEpoR) is cloned into pGEX-2T (Pharmacia, Mechanicsburg, Pa.). pGEX-2T has an IPTG inducible promoter operably linked to a coding sequence for glutathione S-transferase (GST). The 3' end of the GST coding sequence has a thrombin proteolytic cleavage site in the correct reading frame, as well as convenient cloning sites for inserting a coding sequence to be covalently coupled to GST.

A PCR product having amino acids 25 through 250 of hEpoR is made from a suitable DNA template, for example a full-length human EpoR cDNA. A PCR primer is sythesized having the 5' end of the extracellular domain coding sequence as well as a BamH1 site, and a PCR primer is synthesized having sequence complementary to the 3' end of the extracellular domain coding sequence as well as an EcoR1 site. The BamH1 site in pGEX-2T is positioned 5' to the EcoR1 site relative to the GST coding sequence. The PCR product is cloned into pGEX-2T, and a transformed *E. coli* colony having a plasmid of the expected size is identified.

A fusion protein having an amino terminal GST segment and a carboxy terminal EpoR extracellular domain segment is expressed in transformed *E. coli* by inducing transcription with IPTG. IPTG derepresses the lac promoter positioned upstream of the fusion protein coding sequence. After allowing expression for a period of time sufficient to accumulate an amount of the fusion protein, cells are lysed and a crude extract is made in any suitable manner. The crude extract mixture has the fusion protein in addition to many other cellular proteins. The fusion protein, EpoRex-th, may be purified from the extract as desired.

In a preferred embodiment, EpoRex-th is passed over a column having agarose beads coupled to glutathione (GSH). GSH is a substrate for GST, and the GST segment of EpoRex-th will bind to the immobilized GSH with high affinity. Thus, the fusion protein becomes bound to the column, while virtually all other proteins in the extract will not bind. After washing, EpoRex-th may be eluted from the column by adding reduced GSH to the liquid phase.

In an embodiment of the invention, purified human erythropoietin receptor extracellular domain polypeptide may be made by digesting EpoRex-th with thrombin. The resulting digested mixture of GST and Epo-bp may then be applied to an Epo affinity column. The Epo-bp binds to its ligand, Epo, whereas GST passes through the column. Epo-bp may be eluted in purified form through use of an appropriate elution buffer, for example 0.1 M glycine, pH 3.0.

Antibodies to human erythropoietin receptor extracellular domain can be made by presentation of a purified preparation of such a polypeptide to the immune system of an animal. For example, purified Epo-bp may be injected subcutaneously, intramuscularly or intraperitoneally into animals such as rats, mice, rabbits, or sheep. Booster injections can be given at intervals, if desired. Circulating antibodies against Epo-bp are made by the immune system of the injected animal, and these antibodies can be collected from the blood, preferably from the serum. Anti-Epo-bp serum can be used to detect Epo-bp in various assay formats, such as Western blots, ELISA assays and the like. Epo-bp to be detected may be from, for example, a purified preparation of Epo-bp, a bacterial or eukaryotic cell extract, a eukaryotic cell from an in vitro cell culture, a serum sample, or even a tissue or cell biopsy taken from an individual. Anti-Epo-bp antibodies are expected to recognize the extracellular domain of intact human EpoR as well as Epo-bp. Monoclonal antibodies directed against Epo-bp can be made by methods known in the art. D'Andrea et al., *Blood* 75: 874–80 (1990); Goldwasser et al., U.S. Pat. No. 4,558,005; Harlow and Lane, *Antibodies—Lab Manual*, Cold Spring Harbor Laboratory, 1988.

Antibodies directed against Epo-bp preferably have a specific binding affinity for the EpoR extracellular domain. For example, serum from an animal injected with purified Epo-bp should provide detectable binding to Epo-bp in Western blots when 10 µg of purified Epo-bp are electrophoresed in a polyacrylamide gel and exposed to a 1:2000 dilution of the anti-Epo-bp serum.

The purified extracellular domain of EpoR disclosed herein is the first such pure human Epo receptor fragment (i.e., free of non-human or non-Epo receptor amino acid sequence) to be obtained. The experiments disclosed herein demonstrate that such a fragment retains the ability to specifically bind human Epo. The proteins and antibodies disclosed herein are useful for understanding the mechanisms of Epo-Epo receptor interaction. The purified Epo-bp of the present invention is also useful for investigating the structure of the Epo receptor and for identifying factors involved in regulating differentiation and proliferation mechanisms in erythroid progenitor cells. Moreover, the invention disclosed herein is useful for identifying and quantitating Epo and Epo receptor, as well as in understanding hematopoietic malignancy and certain cardiovascular system disorders. That is, increased/decreased hematocrit and/or hemoglobin levels may affect blood pressure and cause other circulatory problems.

The invention will be further understood with reference to the following illustrative embodiments, which are purely exemplary, and should not be taken as limiting the true scope of the present invention as described in the claims.

EXAMPLE 1

Materials

Glutathione (GSH)-agarose, pGEX-2T expression vector and Sephadex G-50 were purchased from Pharmacia (Mechanicsburg, Pa.). PCR reagents were from Perkin-Elmer Cetus (Norwalk, Conn.) and Affigel 15 was from BioRad (Richmond, Calif.). Bacteriophage T4 DNA ligase, restriction enzymes and isopropylthio-β-D-galactoside (IPTG) were purchased from BRL Gibco (Gaithersburg, Md.). Geneclean II was from Bio 101, La Jolla, Calif. Nitrocellulose was from Schleicher & Schuell Co. (Keene, N.H.). Chemiluminescence (ECL) reagents and $^{125}$I-Epo were from Amersham (Arlington Heights, Ill.) and unlabeled Epo was a gift of Chugai-Upjohn (Rosemont, Ill.). Phenylmethylsulfonylfluoride (PMSF), diisopropylfluorophosphate (DFP), thrombin, trypsin and Triton X-100, were from Sigma Chemical Company (St. Louis, Mo.). Biotinylated rabbit anti-sheep antibodies and avidin-horseradish peroxidase were from Pierce Co. (Rockford, Ill.). LAP37, a full-length human erythropoietin receptor (EpoR) cDNA preparation, was provided by Dr. Bernard G. Forget, Yale University, New Haven, Conn. All other chemicals were of reagent grade.

EXAMPLE 2

Construction of EpoR cDNA Recombinant Vector

A recombinant plasmid expression vector, pJYL26, was constructed from a PCR product having the human Epo receptor extracellular domain coding sequence and from the plasmid vector pGEX-2T. The construction of this plasmid is explained below.

PCR amplification was carried out using a full-length human EpoR cDNA, LAP37, SEQ ID NO:4, as a template. The 5'-sense primer (SEQ ID NO:1) was 5'-TTGGATC-CGCGCCCCCGCCTAAC-3'. This primer has a BamH1 linker sequence at the 5' end, followed by the coding sequence for amino acids 25 through 29 of the full length human EpoR protein. The 3'-antisense primer (SEQ ID NO:2) was 5'-TGAATTCGGGGTCCAGGTCGCT-3'. This primer has an EcoR1 linker followed by sequence complementary to the coding sequence for amino acids 250 through 246 of full length EpoR. Using a Perkin Elmer-Cetus PCR kit, PCR was carried out with 0.1 µg of LAP37 (SEQ ID NO:4) cDNA, 20 pM of each primer, 1.25 mM dNTP mixture (dGTP, dCTP, dTTP and dATP), 0.5 µl of Taq polymerase, and 10× buffer supplied in the PCR kit. Amplification was carried out by a PTC-100 Programmable Thermal Controller, (M.J. Research, Inc. Watertown, Mass.), with denaturation at 94° C. for 1 min, annealing at 55° C. for 1 min and extension at 72° C. for 1½ m, repeated for 25 cycles.

The sizes of the PCR product (~600 bp) and pGEX-2T (~4.9 kb) were verified on 1% Seakem and 2% Nusieve agarose (FMC Bioproducts, Rockland, Me.) gels running in 1×TA buffer (50×TA in 1 liter volume containing 242 g Tris-base and 57.1 ml acetic acid), with a Hae II standard. Both the PCR product and pGEX-2T were purified from gel slices by the Geneclean II method as described by the manufacturer (Bio 101, La Jolla, Calif.). Concentrations of the PCR product and pGEX-2T were estimated by absorbance readings at OD260. Both DNAs were then digested with BamH1 and EcoR1 for 4 hours at 37° C. before ligation. The digested products were analyzed on 1% Seakem and 2% Nusieve agarose gels. Both the PCR product and pGEX-2T fragments were cut from the gel and purified again by the Geneclean II method.

The ligation was done in a mixture having 1 µg/µl each of PCR product and pGEX-2T. The mixture was incubated at 45° C. for 5 minutes and chilled to 0° C. Then, in a 10 µl final volume, 1 µl each of 10× bacteriophage T4 DNA buffer and 10× bacteriophage DNA ligase, and 10 mM ATP were added. The whole mixture was then incubated at 16° C. in a circulating water bath overnight. Productive ligation was verified by electrophoresis in a 1% agarose gel in 1×TA buffer running at 100 volts with lanes containing size standards, pGEX-2T, PCR product, and the ligated product (PCR product+pGEX-2T). The ligated product was verified to be ~5.5 kb. An aliquot of ligation mixture was then transformed into E. coli strain JM109 (20 µg ligation mixture/200 µl JM109). For the transformation, the E. coli mixture was incubated on ice for 30 minutes after mixing gently by inverting, and incubated at 42° C. exactly 90 seconds. Then the mixture was chilled on ice for 1–2 minutes and 500 µl LB medium (for 1 liter, 10 g bactotryptone, 5 g bacto-yeast and 10 g NaCl, pH 7.5, autoclave) was added. After incubating at 37° C. for 45 minutes, the LB mixtures were spread on LB/Amp agar petri plates in amounts of 50, 75, 125, 150,and 300 ml of LB mixture. Agar petri plates were prepared with 20–30 ml of LB/Amp medium, containing 15 g agar/liter LB (autoclaved) and 100 µg/liter ampicillin. Control LB/Amp plates were made with intact pGEX-2T, digested pGEX-2T and PCR product only. The plates were kept on the bench top to absorb liquid for a few hours and inverted plates were incubated at 37° C. for 24 hours. Grown colonies were seeded on gridded plates, which were incubated again at 37° C. for 24 hours, while another set of all colonies was grown in 5 ml each of the LB/Amp medium overnight.

The DNA was extracted from each colony by the miniprep method. Each colony was cultured overnight with 5 ml LB/Amp medium (2 µl/ml of 50 µg/ml Amp stock) in a loosely capped 15-ml plastic tube in a vigorously shaking 37° C. incubator. The following day, 1.5 ml of each culture was pelleted in a microfuge for 3 minutes at 4° C. at 14,000×g, and resuspended in 93 µl STET plus 17 µl of lysozyme stock (STET: 5% sucrose+5% Triton X-100+50 mM Tris, pH 8.0+50 mM EDTA, pH 8.0, stored at 4° C.; lysozyme stock: 5 mg/ml, stored in a freezer). The resuspended mixture was then incubated for 10 minutes at room temperature and boiled for 2 minutes before spinning in a microfuge at 4° C. for 15 minutes at 14,000×g. The pellet was removed with a sterile tooth pick, 2 µl of RNAse (100 mg/ml) was added to the supernatant, followed by incubation at 37° C. for 30 minutes. After incubation, 110 µl of ice-cold isopropanol was added and the mixture was inverted 4 times before pelleting at 14,000×g, 4° C. for 15 minute. The pellet (DNA) was then washed with ~1 ml of 70% ethanol to remove residual STET and other contaminants, and the pellet centrifuged again at 14,000×g, 4° C. for 15 minutes. The pellet was then air dried for 1–2 hours and resuspended in 25 µl of sterile dH$_2$O.

The extracted DNAs were verified on a 0.8% agarose gel in TA buffer, running at 100 volts until the front dye line migrated ⅘ of the length of the gel. The gel was stained with ethidium bromide (0.5 µg/ml) at room temperature for 15 minutes on a gentle shaker and destained with dH$_2$O for 15 minutes. DNA bands were examined under UV light. Cultures having DNA of the expected size were examined in 1% agarose gels running in TA buffer after EcoR1 and/or EcoR1 plus BamH1 digestion. The EcoR1 and BamH1 digestion was done by incubating the sample mixture at 37° C. water bath for 2 hours with the mixture of 1 µg of EcoR1 or BamH1 per 2 µg of DNA in 1 µl/10 µl sample volume of 10× reaction buffer provided in the restriction enzyme kit. One colony having a plasmid of about ~5.5 kb in size was selected after examining both EcoR1 and EcoR1 plus BamH1 digested DNA sizes in 1% agarose gels. The plasmid in this colony was named pJYL26. A diagram of pJYL26 is shown in the upper part of FIG. 1.

EXAMPLE 3

Purification of EpoRex-th Fusion Protein

This example teaches the production and purification of a fusion protein having two segments. The first segment is a polypeptide, GST, with a thrombin cleavage site at the carboxyl terminus. The second segment, fused to the first segment at the thrombin cleavage site, is the extracellular domain of human Epo receptor. The fusion protein EpoRex-th, containing GST and Epo-bp, is purified by GSH-agarose affinity chromatography.

Transformed *E. coli* containing the recombinant vector pJYL26 were grown overnight at 37° C. with vigorous shaking in 400 ml of LB medium with 100 μg/ml of ampicillin. The following day, the culture was diluted in 4 liters of fresh LB/Amp media and incubated for another 90 min before adding 1 mM isopropylthio-β-D-galactoside (IPTG). After 4 hours of IPTG induction, the cells were pelleted at 3,000× g at 4° C. for 15 min and resuspended in 160 ml of lysis buffer, containing 50 mM sodium phosphate, pH 7.4, 10 mM β-mercaptoethanol (βME), 10 mM EDTA, pH 8.0, 1 mM PMSF and 1 mM DFP. 160 mg of solid lysozyme was then added. Using a 60 cc syringe, the lysed cell suspension was homogenized by passing through 18, 21 and 23 gauge needles three times, and incubated on ice 30 min. After dry ice/methanol freeze thaw at 37° C. for 3 times and mild sonication, 1% of Triton X-100 was added. The supernatant was collected by centrifugation 15×kg at 4° C. for 15 min.

Figure 2:
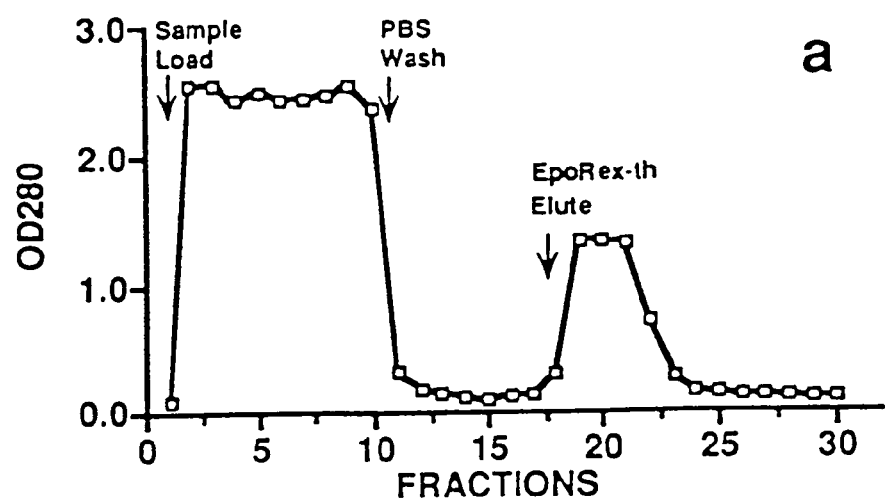
FIG. 2a shows the absorbance at 280 nanometers ($A_{280}$) of fractions collected from purification of an *E. coli* cell extract, expressing EpoRex-th, on a glutathione affinity column.
FIG. 2b shows the $A_{280}$ of fractions containing Epo-bp collected as a result of erythiopoietin affinity chromatography of thrombin treated EpoRex-th.
Figure 2:
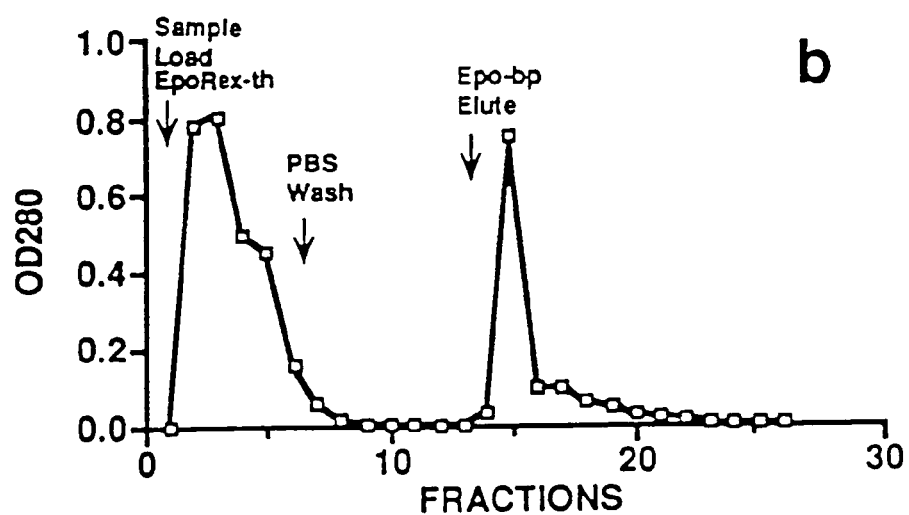

A GSH-agarose column was prepared by washing swollen GSH-agarose beads 3 times with 10 bed volumes of phosphate-buffered saline (PBS: 16 mM $Na_2HPO_4$, 4 mM $NaH_2PO_4$, pH 7.4 in excess salt of 3 M NaCl) to remove preservatives and elutable dextran from the agarose. The column was then equilibrated with 5 bed volumes of isotonic PBS. The IPTG induced extract was applied to the column and the column was washed twice with 5 bed volumes of PBS, which elutes all proteins with no affinity for GSH-agarose. EpoRex-th was then eluted by adding 5 bed volumes of elution buffer, containing 5 mM reduced GSH in 50 mM Tris-HCl, pH 8.0. Fractions of 1.0 ml were collected and the $A_{280}$ was determined for each fraction. FIG. 2a shows the $A_{280}$ data. Fractions 18–23 were subsequently shown to have the EpoRex-th protein. These fractions were pooled. From a four-liter cell culture preparation, an average of 2 mg of EpoRex-th was extracted.

EXAMPLE 4

Purification of Epo-bp

EpoRex-th contains a thrombin-specific proteolytic cleavage site, as diagramed in the lower half of FIG. 1. Thrombin cleaves specifically at the sequence (SEQ ID No. 3) -CTG GTT CCG CGT GGA TCC-, which codes for the amino acids Leu Val Pro Mg Gly Ser, as shown in FIG. 1. Smith and Hohnson, *Gene* 67:31–40 (1988). Thrombin was incubated with EpoRex-th to cleave the GST segment from the Epo-bp segment and the two segments were purified by Epo-agarose affinity, as described below.

Figure 3:
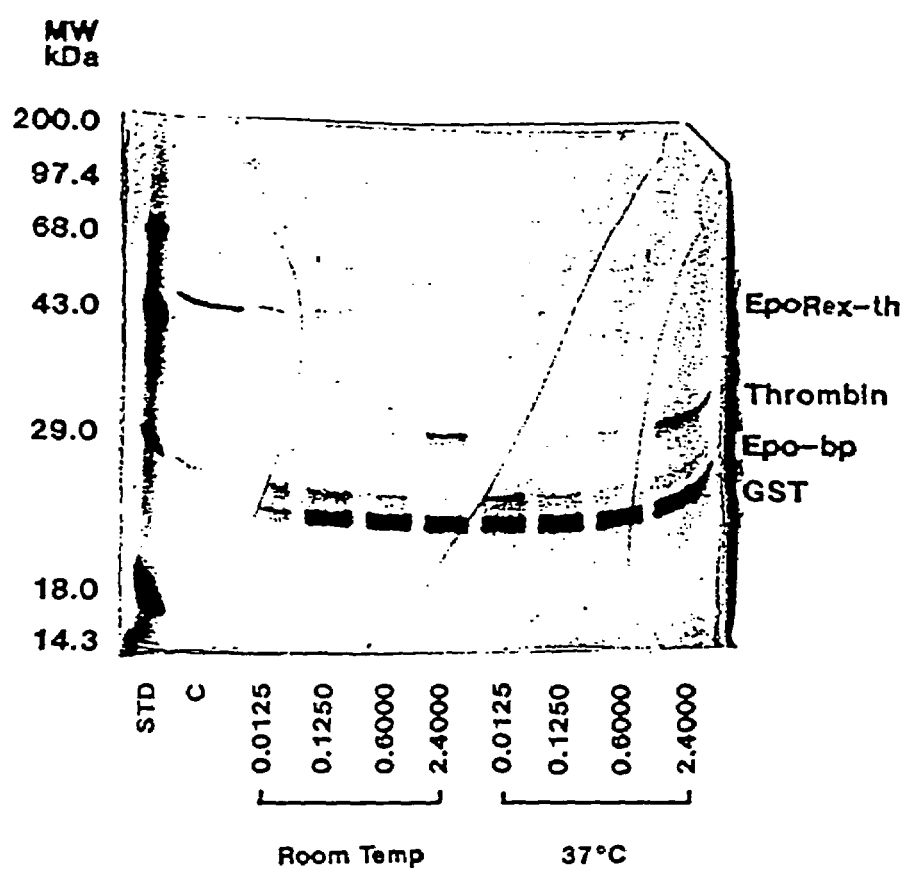
FIG. 3 is a photograph of a Coomassie blue stained polyacrylamide gel, showing the cleavage of EpoRex-th by thrombin.

Various thrombin concentrations were tested in order to find the most effective range of thrombin cleavage. Purified EpoRex-th was incubated with 0.0125, 0.125, 0.6 or 2.4 μg of thrombin per 60 μg EpoRex-th at room temperature or 37° C. for 1 hour in PBS buffer, pH 7.4. The results were analyzed by polyacrylamide gel (12.5%) electrophoresis. After staining with Coomassie blue, bands could be seen corresponding to the fusion protein EpoRex-th (55 kDa), Epo-bp (29 kDa) and GST (26 kDa). The 0.6 μg concentration was selected for complete digestion of EpoRex-th. The results are presented in FIG. 3.

For thrombin cleavage, 60 μg of EpoRex-th was incubated at room temperature for 1 hr with 0.6 μg thrombin. The mixture was applied to an erythropoietin-agarose column in Tris buffered saline (TBS) or PBS. Epo-bp was eluted with 0.1 M glycine buffer, pH 3.0. Fractions of 0.5 ml were collected into tubes, containing 0.5 ml of 2 M Tris-HCl, pH 7.5. Epo-bp peak fractions 14–19 were pooled and then dialyzed overnight in TBS or PBS at 4° C. for further experiments. Approximately 200 μg Epo-bp was extracted, starting from a four-liter cell culture preparation.

The Epo-agarose column was prepared from Epo-agarose beads. The Epo-agarose beads were prepared by overnight dialysis of Epo (0.5 mg/ml) in 0.1 M 3(N-morpholino)-propanesulfonic acid (MOPS) at 4° C. Epo was linked to Affigel 15 beads by admixing 1 ml of the dialyzed Epo-solution and 2 ml of washed Affigel 15, and incubated at room temperature for 2 hours on a rotating shaker. The supernatant was removed after microcentrifuging at 2000×g for 30 sec. The packed Epo-agarose beads were washed 3 times in TBS or PBS at 4° C. and stored until ready to use. After collecting desired protein fractions, Epo-agarose beads may be washed extensively with TBS or PBS and stored at 4° C. for reuse.

EXAMPLE 5

Production of Antibodies to Epo-bp

This example teaches the production of antibodies directed against purified Epo-bp. Purified Epo-bp is electrophoresed in a 12.5% SDS-PAGE gel and the Epo-bp protein band is resuspended in PBS and injected into sheep. Sheep serum having anti-Epo-bp antibody is shown to detect purified human Epo-bp when the serum is diluted 1:2000.

Epo-bp (0.5 mg), purified as described above, was mixed with 2× treatment (Laemmli) buffer and boiled for 10 minutes. The mixture was applied to a 12.5% SDS gel and electrophoresed at 200 volts for 3–4 hours. The gel was stained with 0.125% Coomassie blue overnight, destained 1–2 hours with $dH_2O$, and the Epo-bp band cut out of the gel with a razor blade.

The Epo-bp gel slice was resuspended in 10–15 ml of PBS buffer and passed through a syringe repeatedly until the gel was crushed into small pieces forming a suspension mixture with PBS. The suspension was injected subcutaneously in adult sheep. Epo-bp was injected at a ratio of 0.5 mg Epo-bp or more per 25 kg weight of the animal. Two booster injections, with the same dose as in the initial injection, were given once every 3 weeks following initial injection. After the second booster injection, blood can be withdrawn for collection of antibodies. Injections can be given every month to maintain antibody production by the animal. Injection sites are rotated on the animal. Sambrook et al., *Molecular Cloning*, 2nd Ed., Cold Spring Harbor Laboratory Press, Chapter 18, 1989.

To obtain blood from injected animals, hair at the blood sampling site was cleaned with 70% alcohol. Ear arteries or other accessible arteries were shaved over. A small amount of xylene was applied to the tip of the ear but not at the bleeding site. Blood was gently withdrawn with a butterfly and put into a glass tube having no heparin. The blood was incubated at room temperature for 1 hour to allow clotting, the clot was loosened from the tube wall with a pasteur pipet, and the tube was incubated at 4° C. overnight. The clotted blood mixture was poured into a dish and the clot removed. The unclotted remainder was returned to the glass tube and centrifuged at 3000 rpm for 10 minutes. The supernatant (serum) was applied to an Epo-bp-affinity column and antibodies binding to the column were eluted by with 0.1 M glycine buffer, pH 3.0, using the same procedures as discussed above for purification of Epo-bp. The eluate was dialyzed in PBS overnight at 4° C. and stored at −70° C. in 500 µl aliquots. The Epo-bp affinity column was prepared from Epo-bp and Affigel 15 agarose beads in the same manner as the Epo-bp Affigel beads described in Example 6 below.

Solutions used in this example are prepared as follows:
Lysis Buffer II: 50 mM $NaPO_4$ (7.74 ml of 0.5 M dibasic $PO_4$ plus 2.26 of 0.5 M monobasic $PO_4$) +10 mM β-mercaptoethanol+10 mM EDTA, pH 8.
PBS Buffer: 0.15 M NaCl+16 mM dibasic $PO_{4+6}$ mM monobasic $PO_4$, pH 7.4.
TBS buffer: for 1 liter, 12.5 ml of 2 M Tris-HCl, pH 7.4+27.5 ml of 5 M NaCl.
2× Treatment (Laemmli) buffer: 0.125 M Tris-HCl, pH 6.8+4% SDS+20% glycerol+10% beta-mercaptoethanol.

Sheep anti-Epo-bp serum was analyzed for binding to purified Epo-bp by Western blotting as described in Sambrook et al., *Molecular Cloning*, 2nd Ed., Cold Spring Harbor Laboratory Press, 1989 and in Western blotting protocols provided by the ECL manufacturer, Amersham Co., Arlington Heights, Ill. Following thrombin cleavage, EpoRex-th and Epo-bp were separated electrophoretically on an SDS-PAGE gel. The gel was then blotted onto nitrocellulose (Schleicher and Schuell Co., Keene, N.H.). Sheep anti-Epo-bp serum was added to the nitrocellulose in Blotto (for 1 liter: 80 g non-fat dry milk, 30 ml 5M NaCl, 10 ml 2M Tris-HCl, pH 7.5 and 0.05% Tween-20) at a 1:2000 dilution and incubated at room temperature for 1 hour with gentle agitation. After rinsing off the first antibody, a second reagent, biotinylated rabbit anti-immunoglobulin anti-sheep (1:10,000 dilution) antibody was added to the nitrocellulose in Blotto, and incubated at room temperature for another 1 hour with rocking. Horseradish peroxidase-avidin (1:10,000 dilution) was added and the mixture incubated at room temperature for 45 min. After soaking the washed nitrocellulose briefly in chemiluminescence (ECL) reagents, wet blots were exposed immediately on KODAK X-ray film. FIG. 4 shows a photograph of the Western blot, with the lanes having the following proteins applied: Lane 1, molecular weight standards; Lane 2, thrombin digested EpoRex-th; Lane 3, GST; Lane 4, purified Epo-bp. As shown in lane 4 of FIG. 4, purified Epo-bp was detected by a 1:2000 dilution of anti-Epo-bp antibody. The apparent molecular weight of the purified Epo-bp was about 29 kDa.

EXAMPLE 6

Binding of Epo to Epo-bp

Ligand binding of Epo to Epo-bp and effects of Epo concentration on binding are taught in this example.

Epo-bp beads were prepared by adding 60 µg/ml Epo-bp to washed Affigel 15 agarose beads in PBS, with a final concentration of approximately 30 µg of protein per 1 ml of Epo-bp beads. The mixture was incubated at room temperature for 2 hours on a rotating platform. After washing 3 times with ice cold PBS buffer, the pellet was resuspended in 1 ml of PBS buffer. For binding assays, 30 ul of the final suspension (approximately 1.0 µg of Epo-bp) were admixed with various concentrations of $^{125}$I-Epo and incubated for 1 hour at room temperature while resuspending every 5 min with a pipet. At the end of the incubation, 1 ml of ice cold PBS buffer was added to wash out unreacted $^{125}$I-Epo and the wash was repeated twice more. The reacted beads were counted by a gamma counter. Proteins smaller than the intact Epo-bp from trypsin digested extracts (see below) were also applied in the same way to test any effect on ligand binding. Nonspecific binding was measured by the same method except the mixture was preincubated with a 200-fold excess of unlabeled Epo for 1 hour prior to adding labeled Epo.

Figure 5:
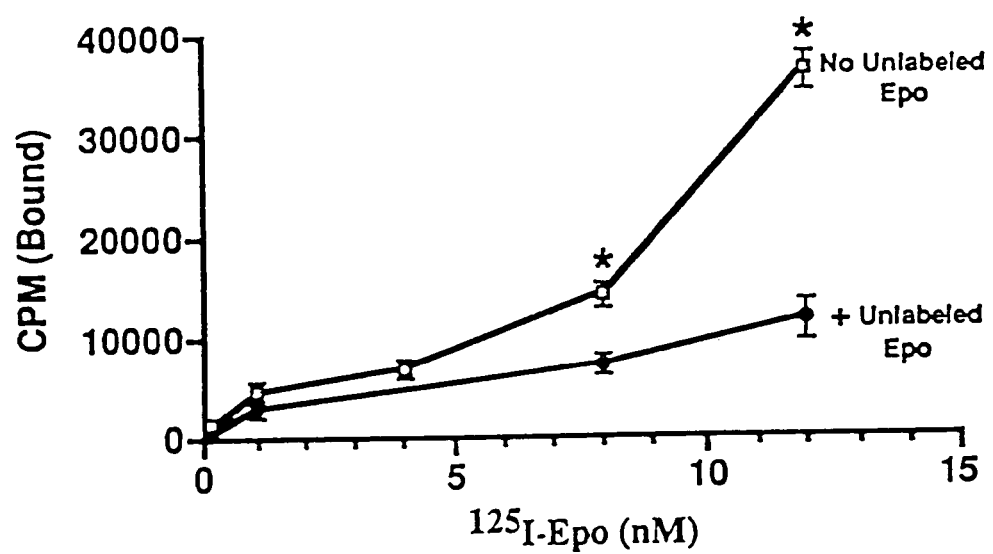
FIG. 5 shows the binding of various concentrations of human $^{125}$I-Epo to Epo-bp, in the presence and absence of unlabeled Epo.

Binding of Epo-bp to Epo is shown in FIG. 5. Each point in FIG. 5 is the mean of 2–4 samples. Data are expressed as mean±SEM. A p value of less than 0.05 was considered significant. Results were analysed with the two-tailed Student t-test. The specific binding activity of Epo to Epo-bp dramatically increased as Epo concentration increased; the binding tripled from 8 nM to 12 nM $^{125}$I-Epo. Apparent saturation of Epo binding occurred at 12 nM. This was also confirmed in the unreacted supernatant of $^{125}$I-Epo. Binding of $^{125}$I-Epo to Epo-bp was significantly inhibited in the presence of unlabeled Epo at concentrations of 8 nM and higher of $^{125}$O-Epo ($p<0.0001$ in both comparisons). Nonspecific binding was somewhat higher than expected. It had been expected that the excess unlabeled Epo might eliminate $^{125}$I-Epo binding completely because of the sensitivity and specificity of Epo binding to Epo-bp shown in Western blots and binding assays.

Figure 6:
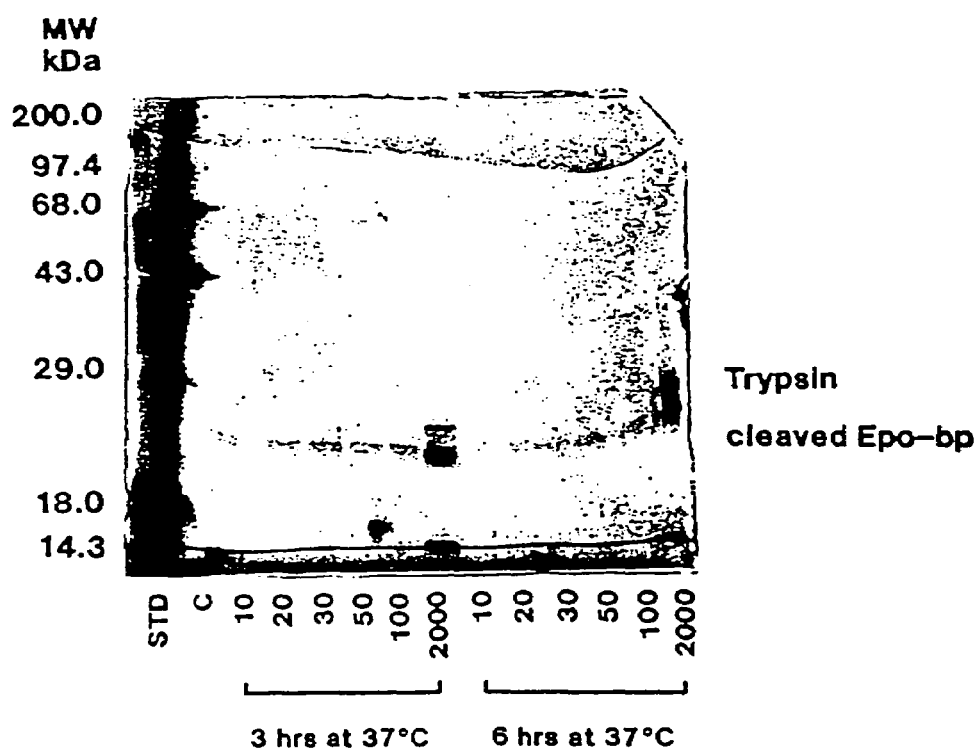
FIG. 6 is a photograph of a Coomassie blue stained polyacrylamide gel, showing the polypeptide bands observed after trypsin digestion of Epo-bp.

Trypsin digestion experiments were performed to find a minimum sequence of Epo-bp involved in ligand binding. There are several arginine and lysine sites in the Epo receptor protein, which may be specific sites for trypsin digestion. Trypsin digestion of Epo-bp was carried out at 10, 20, 30, 50, 100 µg and 2 mg of trypsin per 5 µg of Epo-bp in a total volume of 200 µl in PBS, pH 6.7 at 37° C. for 3 or 6 hours. The reaction was stopped by adding the same volume of 2 N acetic acid or by boiling. As shown in FIG. 6, Epo-bp was cleaved effectively when 20 µg or more of trypsin was present. Trypsin is visible as a 23.2 kDa protein band in the lane having 2 mg of trypsin. The trypsin digested Epo-bp is visible as a 20-kDa protein. In FIG. 6, Lane 1 contains standard molecular weight markers; lane 2 is a control; lanes 3–8 represent digestions at concentrations of 10, 20, 30, 50, 100 µg and 2 mg trypsin, respectively at 37° C. for 3 hours; lanes 9–14 represent the same concentrations of trypsin incubated at 37° C. for 6 hours.

Since uncut Epo-bp is aproximately 30 kDa, gel filtration chromatography using Pharmacia Sephadex G-50 (MW≦30,000) was applied to separate protein components of size≦30,000 molecular weight from the total mixture. A powdered form of Sephadex G-50 was hydrated and washed several times with isotonic PBS to wash out preservatives. Trypsin digested EpoRex-th was applied to the top of the gel column in a total volume of 0.2 ml in PBS. The column was centrifuged at 2,000×g for 4 min at room temperature in a swinging-bucket rotor. The first effluent was collected from the bottom of the syringe (~0.2 ml) into a decapped microfuge tube. This effluent contains proteins having a size larger than Epo-bp. Another 0.2 ml of PBS buffer was added to the column and a second eluate collected into a new decapped microfuge by recentrifuging for 10 min. This step was repeated twice. The second eluate was applied to an Epo-agarose column and peak fractions were examined by SDS-PAGE gels and Western blotting. The final product of Epo-bp, as a result of trypsin digestion, was approximately 20 kDa, shown in FIG. 6. The antibody did not recognize the cleaved Epo-bp. Thus, deletion of 30 amino acids from Epo-bp by trypsin digestion completely eliminated recognition by antibodies to Epo-bp, as verified by Western blotting.

The foregoing detailed description has been provided for a better understanding of the invention only and no unnecessary limitation should be understood therefrom as some modifications will be apparent to those skilled in the art without deviating from the spirit and scope of the appended claims.

I claim:

1. An isolated polypeptide consisting essentially of about amino acid 25 to about amino acid 250 of a full length human erythropoietin receptor protein (SEQ ID NO:5), said polypeptide having a specific affinity for human erythropoietin, wherein said polypeptide has a molecular weight of 29 kDa.

2. A binding assay composition comprising:
(a) a solid phase reagent; and
(b) the polypeptide of claim 1 operably coupled to said reagent.

3. A method for obtaining an antibody having specific binding affinity for human erythropoietin receptor polypeptide, said method comprising:
contacting a non-human mammal with a purified preparation of an extracellular domain fragment of human erythropoietin receptor polypeptide consisting essentially of about amino arid 25 to about amino acid 250 of a full length human erythropoietin receptor protein (SEQ ID NO:5), said polypeptide having a specific affinity for human erythropoietin, wherein said polypeptide has a molecular weight of 29 kDa, and collecting said antibody from said non-human animal.

4. The polypeptide of claim 1 wherein the full length human erythropoietin receptor protein is encoded by a full length human erythropoietin receptor DNA (SEQ ID NO:4 and the polypeptide consisting essentially of about amino acid 25 to about amino acid 250 of the full length human erythropoietin receptor protein corresponds to the region of the full length human erythropoietin receptor DNA defined on the 5' end by a forward primer SEQ ID NO:1 and defined at the 3' end by reverse primer SEQ ID NO:2.

5. An isolated polypeptide consisting of a human erythropoietin receptor extracellular domain, said polypeptide having a specific affinity for human erythropoietin, wherein the human erythropoietin receptor extracellular domain is expressed from a region of a full length human erythropoietin receptor DNA (SEQ ID NO:4) defined on the 5' end by a forward primer SEQ ID NO:1 and defined at the 3' end by a reverse primer SEQ ID NO:2.

* * * * *